United States Patent [19]

Rishton

[11] 4,116,589
[45] Sep. 26, 1978

[54] EXTRACORPOREAL PULSATILE BLOOD PUMP COMPRISED OF SIDE BY SIDE BLADDERS

[75] Inventor: Michael L. Rishton, Reading, Mass.

[73] Assignee: Avco Corporation, Everett, Mass.

[21] Appl. No.: 787,787

[22] Filed: Apr. 15, 1977

[51] Int. Cl.² .......................... F04B 9/12; F04B 43/08
[52] U.S. Cl. .................................. 417/384; 417/385; 417/389; 417/394; 128/214 F
[58] Field of Search ............... 417/384, 388, 389, 394, 417/478, 479, 385; 92/50, 92, 93; 128/214 F, DIG. 3; 222/95

[56] References Cited

U.S. PATENT DOCUMENTS

| | | | |
|---|---|---|---|
| 2,700,340 | 1/1955 | Wood | 417/384 |
| 2,827,853 | 3/1958 | Bradley | 417/389 |
| 3,134,304 | 5/1964 | Hager | 417/401 |
| 3,478,695 | 11/1969 | Goranson et al. | 417/394 |
| 3,811,800 | 5/1974 | Shill | 417/394 |
| 3,816,032 | 6/1974 | Flynn et al. | 417/389 |
| 3,895,741 | 7/1975 | Nugent | 128/214 F |

FOREIGN PATENT DOCUMENTS 2,402,056 7/1975 Fed. Rep. of Germany ........... 417/388

Primary Examiner—Carlton R. Croyle
Assistant Examiner—Thomas I. Ross
Attorney, Agent, or Firm—Melvin E. Frederick

[57] ABSTRACT

Extracorporeal blood pumping apparatus for use, for example in cardiopulmonary bypass procedures, left ventricle assist, hemodialysis and the like. The pulsatile pump apparatus may comprise an elongated driver balloon and a similar blood pumping balloon positioned side by side in a rigid casing or housing having preferably a one-way air valve. The inlet and/or outlets of both balloons are off-set and sloping ballon end portions are provided, inter alia, to minimize folding and/or rubbing during use. The driver balloon is provided with a port for coupling to a pressure-vacuum source and the blood pumping balloon is provided with an inlet port and an outlet port and both balloons are of such a cross sectional size and construction as to provide non-occlusive action by the blood pumping balloon. The one-way valve in the housing permits the reduction of deflation time of the driver balloon when it is coupled to a vacuum source, the provision of counterpulsation, prevents the introduction of gas into the blood stream in the event of a failure of the blood pumping balloon and prevents actuation of the blood pumping balloon in the event of failure of the driver balloon.

8 Claims, 11 Drawing Figures

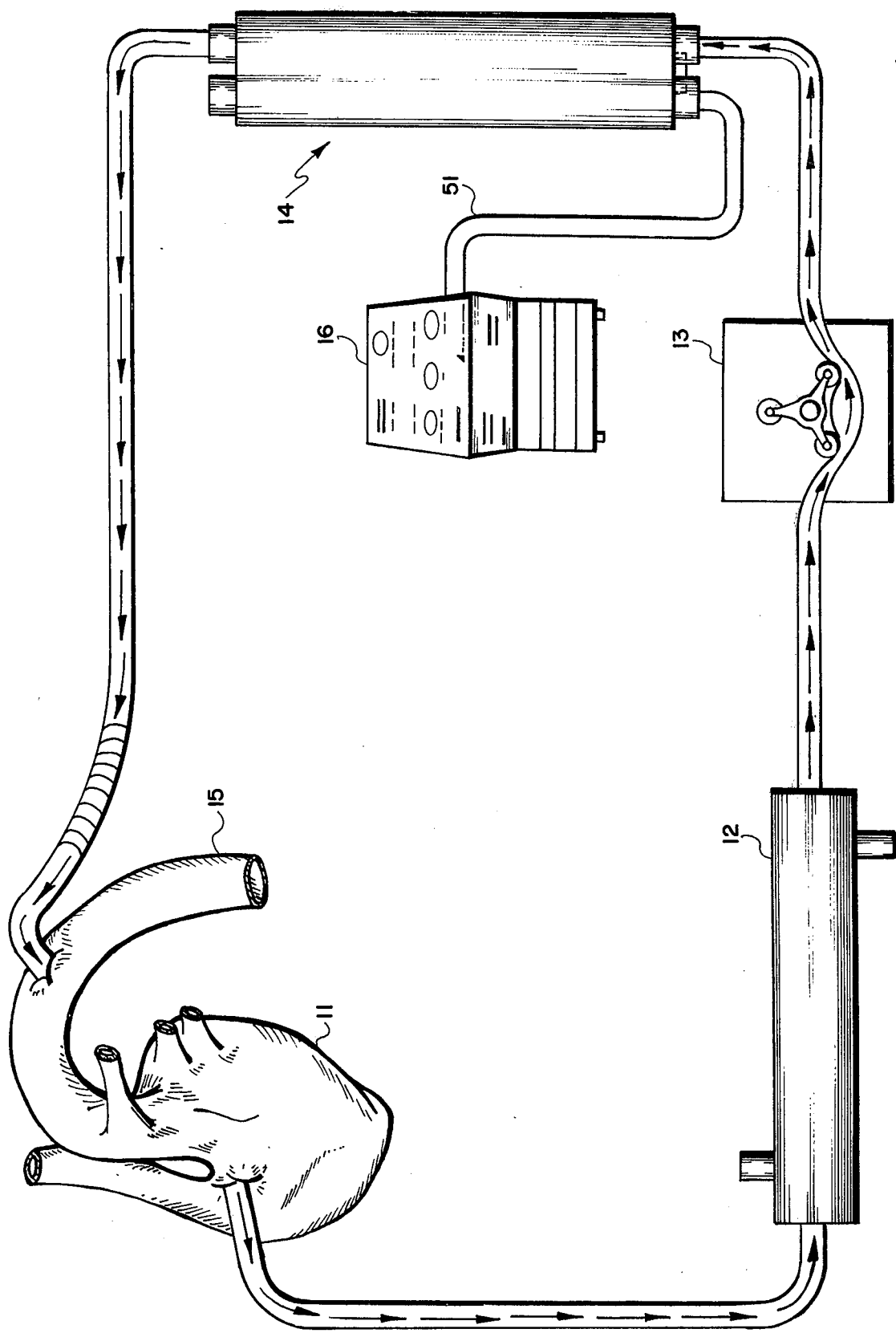

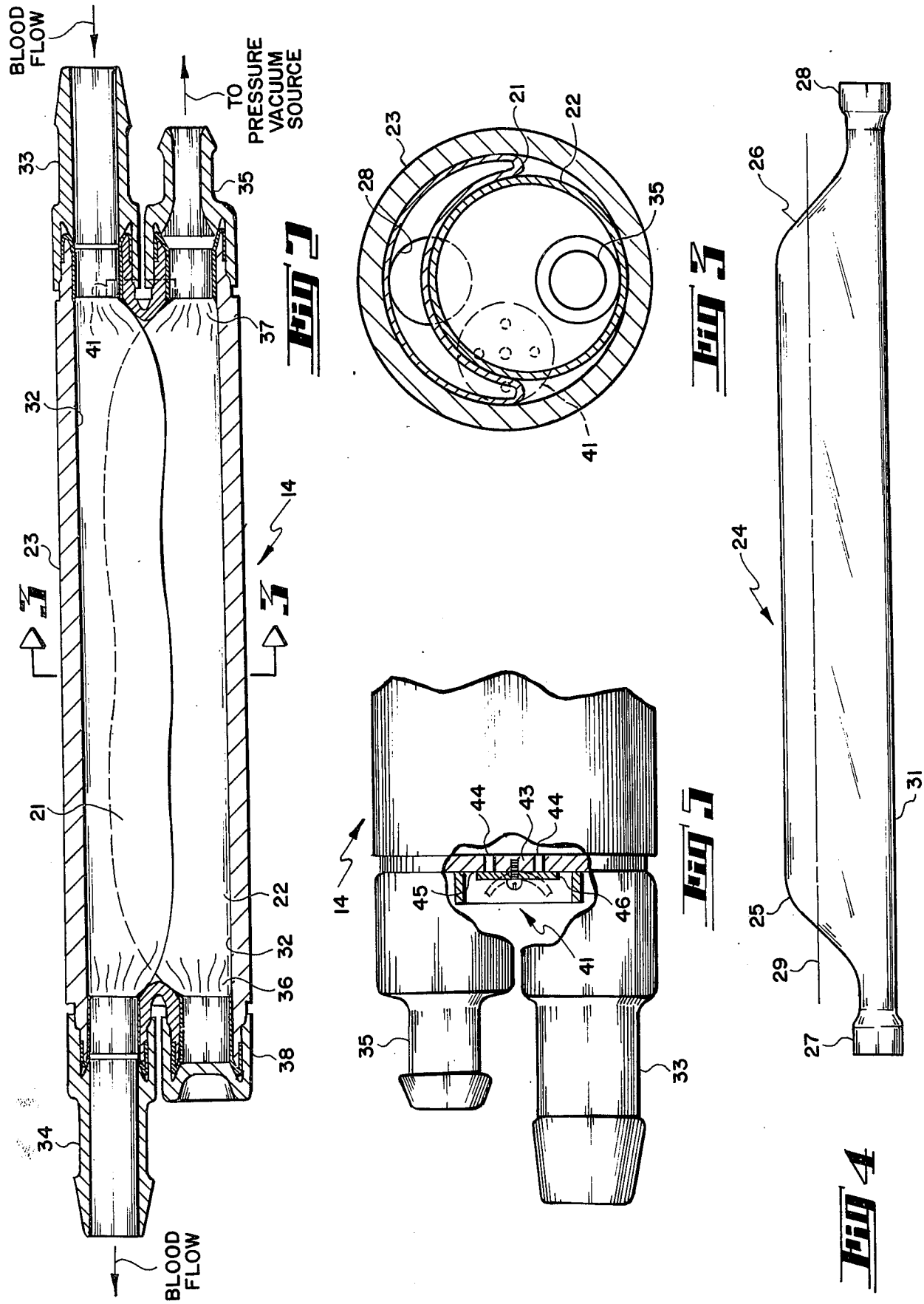

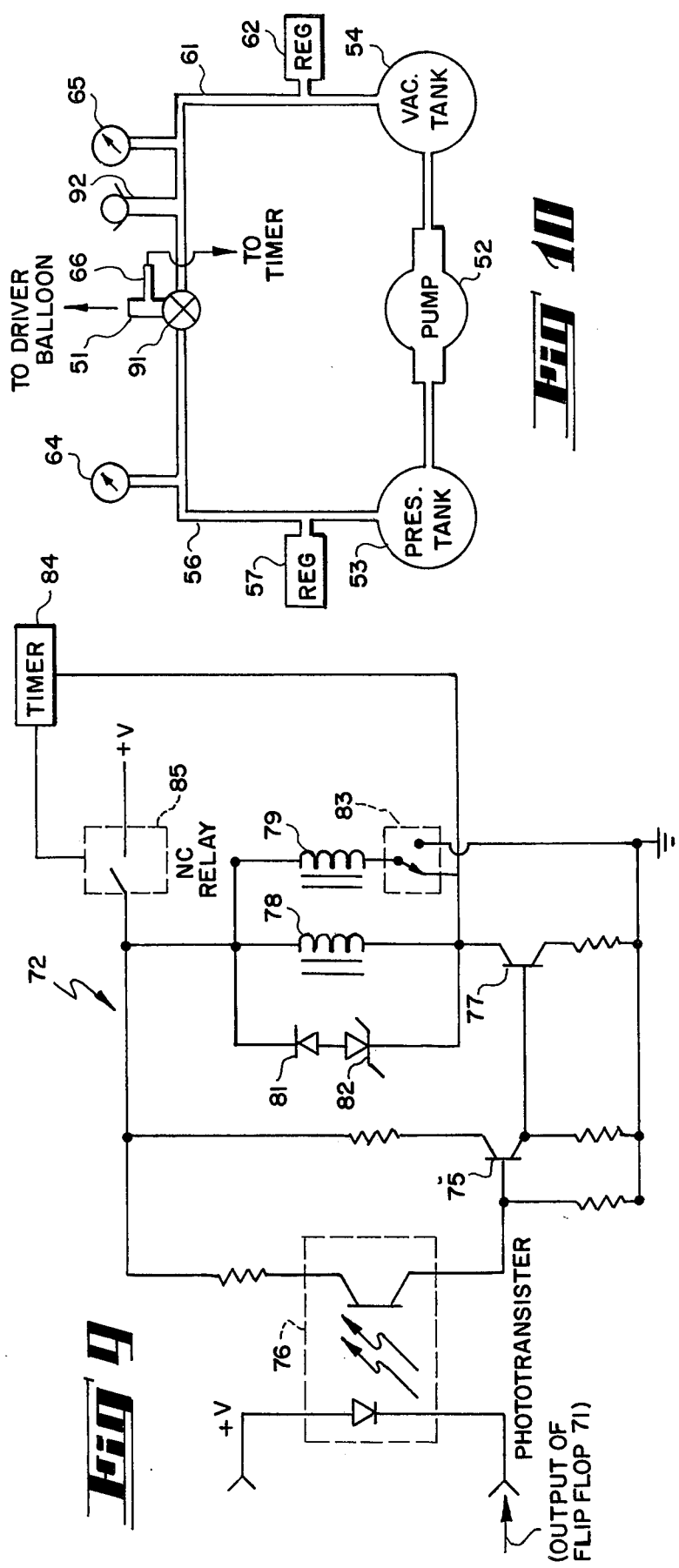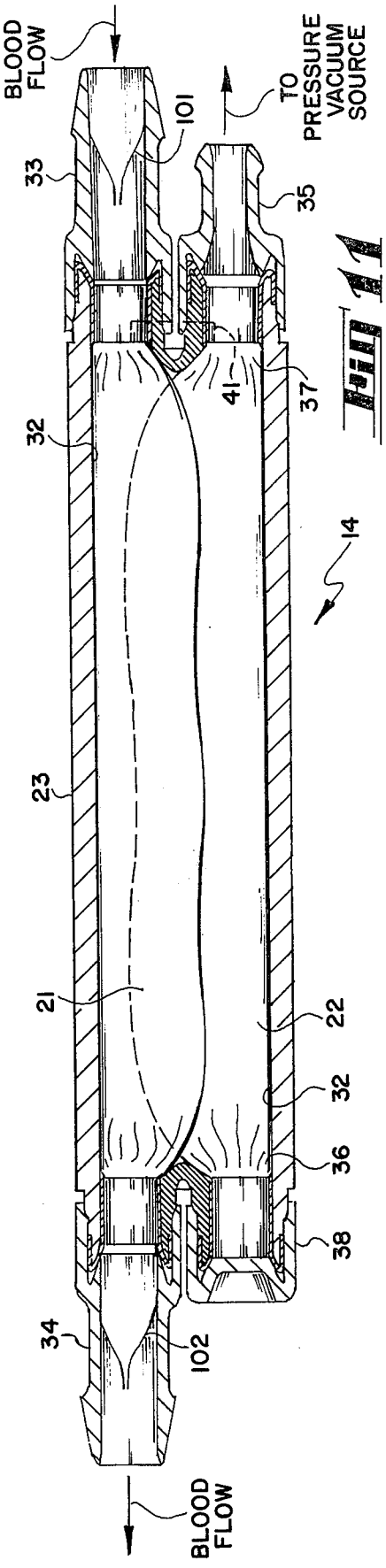

EXTRACORPOREAL PULSATILE BLOOD PUMP COMPRISED OF SIDE BY SIDE BLADDERS

The present invention relates to pumping systems and, more particularly, to a non-occlusive pumping system for use as a substitute or assistive extracorporeal non-occlusive blood pumping apparatus.

During open-heart surgery or in applications where it is desired to assist the circulatory function of a failing heart, blood is removed from the body of a patient at a low pressure level and is pumped into the arterial system at a higher pressure. Quite often, portions of the normal circulatory system are bypassed in this manner to permit surgery to be performed upon the affected parts or organs such as, for example, the heart itself. Typically, this is achieved primarily through the use of a roller pump. The characteristics of a roller pump are such as to progressively compress an elongated length of tubing which acts as a conduit for blood flow through the use of several rollers rollingly and compressingly engaging the tubing in a successive fashion so as to force the blood through the tube and thereby either replace or supplement the natural heart function.

The roller pump comprises the main pump portion of equipment used in open-heart surgery and known as pump-oxygenators or heart-lung machines. Pump-oxygenators or heart-lung machines function in place of a patient's lungs and heart while surgery is being performed. Pump-oxygenator equipment typically comprises a combination of pumps and other devices necessary for the proper functioning of the complete system. In prior known pump-oxygenator equipment used in cardiac surgery, the pump oxygenator may include a venous reservoir, a coronary sinus reservoir, various types of pumps, bubble traps, filters, heat exchangers and other similar devices. Thus, in a typical system utilized in cardiac surgery heretofore, the following units may have been employed: a roller pump for maintaining the arterial circulation; a pump for pumping from a venous reservoir into an oxygenator; a pump for maintaining coronary circulation during the operation; a coronary sinus pump, together with one or another of the various types of oxygenators; a suitable venous reservoir; a suitable filter and bubble trap; and means for maintaining constant temperatures or for reducing the temperature of the blood, if necessary.

The roller pump provides essentially a steady flow, albeit that a small amount of "ripple" or variation in pressure is present, and as of the present, is the standard pump used in cardiopulmonary bypass procedures. While a large number of pulsatile pumps and pumping techniques have been developed, they have not gained acceptance because of their complexity, hazards, high line pressures, excessive hemolysis and the like. The aforementioned pumps and techniques have been developed because it has been found that in cardiopulmonary bypass procedures, pulsatile flow, at least for total body profusion or isolated organ profusion, is preferred over nonpulsatile flow as typically provided by the roller pump.

Although widely accepted, the conventional roller pump used during cardiopulmonary bypass is not without hazards to the patient. For short profusions such as, for example, for durations of 1 to 1½ hours, patients appear to tolerate the procedure quite well. Profusion periods of greater duration as noted above pose a sense of uneasiness among some cardiac surgeons because of potential increase in morbidity and mortality rates. Adverse affects of prolonged procedures utilizing the roller pump have been documented and described in the literature. Further, it has been recognized that pulsatile profusion is better physiologically for the organs and for the microcirculation than the steady flow delivered by roller pumps and the like.

As will now be seen, it is important to provide a pumping system which as closely as possible emulates the operation of the natural heart, not only during the time surgery is being performed, but also when it is desired to terminate or begin termination of the use of the bypass procedure and have the heart again take over its natural functions.

The present invention, which accomplishes the above by the provision of pulsatile flow and counterpulsation, may comprise an elongated driver balloon and a similar blood pumping balloon positioned side by side in a rigid housing preferably having a one-way air valve that permits only air flow out of the housing. Ports of both balloons are off-set and sloping balloon end portions are provided to minimize folding and/or rubbing between the balloons during use. The driver balloon is provided with a port for coupling to a pressure-vacuum source and the blood pumping balloon is provided with an inlet port and an outlet port and both balloons are of such a cross sectional size and construction as to provide non-occlusive action by the blood pumping balloon. When used in the assistive mode, one-way valves in or associated with the blood pumping balloon are not necessary. The one-way air valve in the housing permits the reduction of deflation time of the driver balloon when it is coupled to a vacuum source, the provision of counterpulsation, prevents the introduction of gas into the blood stream in the event of failure of the blood pumping balloon and prevents actuation or substantial compression of the blood pumping balloon in the event of failure of the driver balloon.

Accordingly, it is an object of the present invention to provide a pump that is used primarily for the extracorporeal circulation of blood.

Another object of the present invention is to provide a heart pump that is simple in construction and that is atraumatic.

Still another object of the present invention is to provide a pumping apparatus that is capable of being synchronized with the patient's heart.

Still another object of the present invention is to provide a pumping apparatus that is capable of being phased with the patient's heart, the diastolic and systolic cycle of the pumping apparatus being adjustable as desired.

Still another object of the present invention is to provide a pumping apparatus that is simple, lightweight, and that incorporates fail-safe features for converting a steady extracorporeal blood flow into pulsatile flow.

Still another object of the present invention is to provide a pumping apparatus for converting a steady extracorporeal flow of blood into a pulsatile flow which can be synchronized with a patient's heart beat to provide counterpulsation operation, as when a bypass procedure is being terminated and the natural heart action reinstated.

The novel features that are considered characteristic of the invention are set forth in the appended claims; the invention itself, however, both as to its organization and method of operation, together with additional objects and advantages thereof, will best be understood from the following description of a specific embodiment when read in conjunction with the accompanying drawings, in which:

FIG. 1 is a simplified diagrammatic view showing a total bypass system incorporating the present invention in the assistive mode;

FIG. 2 is a sectional side view showing a pulsatile pump in accordance with the invention for assistive mode operation;

FIG. 3 is a sectional end view taken on line 3—3 of FIG. 2;

FIG. 4 is a side view of a balloon in accordance with the invention;

FIG. 5 is a fragmentary sectional side view of the one-way air valve in the housing of the pulsatile pump;

FIG. 9 is a schematic diagram of the valve driver circuit shown in FIG. 8;

FIG. 10 is a diagrammatic representation of an alternate pressure system for use with the pulsatile pump; and FIG. 11 is a sectional side view showing a modification of the pulsatile pump in accordance with the invention inlet and/or outlet valves for providing counterpulsation or use as a pump.

Figure 6:
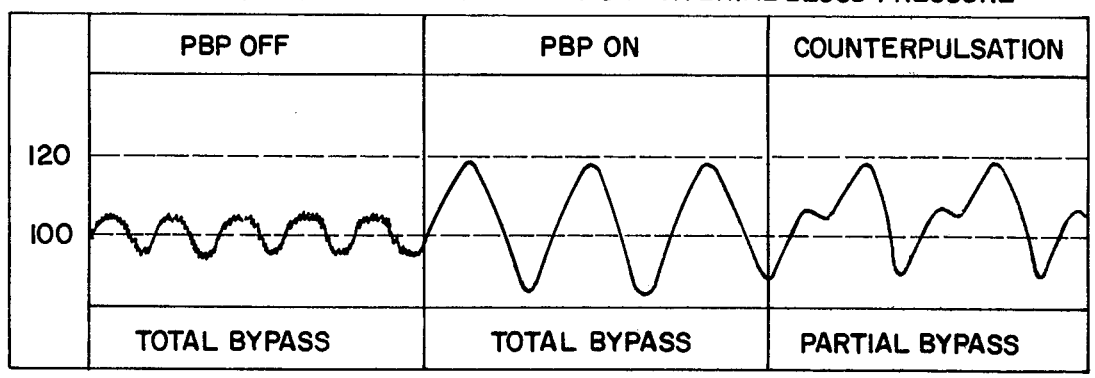
FIG. 6 is a graphic representation illustrating in a bypass system from left to right pressure variation of a roller pump without assistance, pressure variation of a roller pump with assistance in accordance with the invention during total bypass, and pressure variation with assistance in accordance with the invention during partial bypass.

FIG. 1 illustrates a total bypass system incorporating a pulsatile blood pump in accordance with the invention. As shown therein, blood is taken from the right side of the heart 11 of a patient and passes through an oxygenator 12 provided to oxygenate the blood as a substitute for the functions normally performed by the patient's lungs due to the fact that the lungs have been bypassed. The oxygenator 12 replenishes the oxygen in the blood. A conventional roller pump 13 receives blood from the oxygenator 12 and supplies it to a pulsatile blood pump 14 in accordance with the invention and more fully described hereinafter.

The output blood flow of the pulsatile pump 14 is supplied to the arterial system 15 of the patient. Various other conventional components such as, for example, a heat exchanger, reservoirs, bubble traps, filters and the like normally forming part of a heart-lung machine have been omitted for purposes of convenience.

The pulsatile pump 14 as more fully described hereinafter is preferably coupled to and controlled by a conventional console 16 such as, for example, the Avco Intra-Aortic Balloon Pump Model IABP-7 or, if desired, ancillary control apparatus providing equivalent control of pressure, pulse length and frequency, synchronization with a patient's heart beat and the like. Such well-known control and/or apparatus therefor form no part of the present invention.

The pulsatile pump 14 is shown in sectional side view in FIG. 2 and comprises two preferably at least substantial non-distensible elongated balloons 21 and 22 positioned side by side lengthwise in a rigid cylindrical preferably transparent housing 23. For the embodiment shown in FIG. 2, the balloons have the configuration as illustrated in FIGS. 3 and 4. Thus, as shown in FIGS. 3 and 4, the central portion 24 of each balloon is cylindrical. The end portions 25 and 26 of the balloons are respectively curved and sloping and provide such a transition from the cylindrical central portion 24 to cylindrical ports 27 and 28 offset from the longitudinal axis 29 of the balloon. Each port 27 and 28 is coextensive with one side 31 of the balloon as best shown in FIG. 4. The blood pumping balloon 21 is disposed in the housing with its sloping end portions facing away from the interior surface 32 of the housing 23 and its ports are sealably attached as in an overlapping and clenching manner to the housing 23 as by connectors 33 and 34 as shown in FIG. 2. The balloons are made of a preferably translucent or transparent flexible non-stretching plastic material, or at least such a material having a low degree of elasticity, especially in the case of the driver balloon 22. While the driver balloon 22 need not be formed of a material having a surface compatible with blood, such is not the case for the blood pumping balloon 21. The blood pumping balloon 21 preferably is formed of a material or at least has an inner surface compatible with blood so as not to have any effect upon the composition or characteristics of the blood or cause clotting as a result of physical contact therebetween. One such suitable material for the blood pumping balloon is disclosed in U.S. Pat. No. 3,562,352.

The driver balloon 22 is disposed in the housing 23 with its sloping end portions facing those of the blood pumping balloon 21. One end of the driver balloon is sealably attached to the housing as by connector 35 in the same manner as that provided for the inlet and outlet ports of the blood pumping balloon. Connector 35 for the driver balloon is adapted for connection to a pressure line coupled to a suitable pressure-vacuum source.

The end 36 of the driver balloon 22 remote from its inlet port 37 is sealably and fixedly attached to the housing by a cap 38. In the embodiment illustrated in FIG. 2, the driver balloon 22 is provided with two oppositely disposed ports for purposes of convenience in manufacture of the balloons and to provide means for fixedly attaching the remote end of the driver balloon to the housing to prevent longitudinal movement of the driver balloon within the housing during use. It is important that both ends of the driver balloon be fixedly connected to the housing to insure that there is only inflation and deflation movement during use, i.e., the driver balloon does not move longitudinally with respect to the blood pumping balloon and result in undesirable rubbing therebetween. Minimum rubbing and friction between the balloons is insured by not only preventing movement of the ends of the balloons, but also by their sloping end portions which are in face-to-face relationship.

The sloping end portions of the balloons result in a rolling action between the balloons at this region as they expand and contract during use. The transition region represented by the sloping end portions is of particular significance as the provision of such regions avoids folding (and, hence, fatigue), rubbing, or sticking. Should there be a tendency of the balloons to stick together during use, this can cause stretch-fatigue and, hence, possible early failure.

Both of the balloons are provided with a diameter slightly less than that of the interior diameter of the housing as illustrated in FIG. 3. This prevents creasing or folding, occlusive action of the blood pumping balloon and contact (and possible sticking) of the upper and lower portions of the interior of the driver balloon due to the action of the blood pumping balloon.

While a particular manner of sealably anchoring the remote end of the driver balloon has been shown and described, other techniques will be obvious to those skilled in the art and are considered to be included within the scope of the invention.

Directing attention now to FIG. 5, there is shown in detail the one-way air valve 41. As shown in FIG. 5 by way of example, the one-way air valve 41 may comprise an end wall 43 having a plurality of openings 44 disposed around a central axis. Closing the openings 44 and disposed on the exterior surface 45 of the end wall 43 is a flexible member 46 adaptable to cover and seal the openings 44 when the pressure inside the housing is less than ambient pressure (when the driver balloon is collapsing) and to permit the escape of gas from the interior of the housing when the pressure inside the housing exceeds ambient pressure as, for example, when the driver balloon is expanding and/or has ruptured during use.

As shown in FIG. 1, the driver balloon is connected to a line 51 which, in turn, is connected to a pressure-vacuum source in which a suitable gas such as air or a non-toxic, non-inflammable gas such as helium may be maintained at pressure, vented to the atmosphere or vented and simultaneously connected to a plenum which is maintained at subatmospheric pressure. Thus, the driver balloon may be pressurized and inflated and depressurized and deflated. The blood pumping balloon carries the blood being pumped externally under pressure provided by a roller pump or the like. When the driver balloon is pressurized, it expands in a rolling manner and exerts pressure against the blood carrying balloon and causes the blood carrying balloon to deflate in a rolling manner. The deflation of the blood pumping balloon, that is, the non-occlusive squeezing of the blood carrying balloon, while it does not change the average rate of flow that is determined by the roller pump, propels the blood forward and away from the roller pump, increasing the line pressure.

As the driver balloon is deflated, the blood carrying balloon is inflated by the pressure exerted by the roller pump. In sufficient vacuum is applied to the driver balloon during deflation, the pressure in the housing but exterior of the balloons may be expected to drop below atmospheric and some back flow into the blood carrying balloon to result, thereby providing a drop or leveling in pressure provided by the blood pumping balloon.

As each balloon rollingly inflates, the volume occupied by it in the cylindrical housing increases as the volume occupied by the other balloon decreases. If this results in an increase in pressure in the housing, the flexible member 46 forming part of the one-way air valve opens and allows the pressure to return to atmospheric. On the other hand, if the pressure inside the housing falls below atmospheric as it may during a vacuum-assisted deflation cycle, due to the fact that the driver balloon collapses more rapidly than the blood pumping balloon expands, the flexible member 46 closes and prevents the pressure in the housing from increasing to atmospheric. Because the pressure within the housing is now lower than atmospheric, the blood carrying balloon inflates more rapidly than it would otherwise, typically pulling blood from the patient, since an increased flow from the roller pump is not possible.

As may now be seen, the air valve 41 thus may serve two functions—one is that it contributes to the speed of the deflation of the driver balloon and the concomitant inflation of the blood carrying balloon; and the second, since the pressure in the housing cannot exceed atmospheric, in the event of one or more balloon failures, gas will not be forced into the blood stream.

It is to be understood that the present invention also contemplates that in air valve 41, the flexible member 46 may be omitted where desired whereby the interior of housing 23 is in continuous communication with the atmosphere via openings 44. In this event, all of the previously described advantages of air valve 41 are provided with the exception of the capability of providing subatmospheric pressure within the housing, and the results thereof during deflation of the driver balloon as may be preferred by some physicians.

The housing is preferably made of transparent polycarbonate. Polycarbonate meets the requirement of not only ease of manufacture, but also storability, that is, it can be stored for extended periods of time without exuding a material such as one of its constituents or one of the chemicals used in its manufacture which would adversely affect the balloons.

There are a number of possible combinations of modes of operation of the pulsatile pump as shown in FIG. 2; a total bypass mode with and without vacuum-assist deflation of the driver balloon, and partial bypass (with and without vacuum-assist) with the pulsatile pump synchronized to the EKG, the pressure trace or a heart pacer. In all of the modes, the console or other suitable ancillary apparatus generates stop and start signals. Thus, in the total bypass mode, the attending physician can set the pulse rate and the interval between the stop pulse and the next start pulse. When the pulsatile pump is synchronized with the EKG, the physician typically cannot set the interval between successive start pulses, but as with the aforementioned Model IABP-7, he can set the interval between the R-wave and the start pulse and the interval between start and stop pulses. The physician is also able to adjust the timing of the start of the pulsatile pump with respect to some characteristic of the pressure pulse and the duration of the pulse itself. This is also the case when the pulsatile pump is synchronized with a heart pacer.

FIG. 6 shows from left to right by way of illustration small variations in pressure provided by a typical prior art roller pump without assistance in the total bypass mode, the significant variations in pressure provided by the pulsatile pump 14 during total cardiopulmonary bypass, and the still significant variation in pressure when assisted by the pulsatile pump 14 during partial bypass when the patient's heart is functioning. During partial bypass, the pulsatile pump 14 as shown in FIG. 6 simulates the effect provided by a conventional intra-aortic balloon pump physically and operatively disposed in the aorta, thereby relieving at least some of the strain on the heart and assisting it in resuming its normal action during the terminal stage of open-heart surgery and the like.

Figure 7:
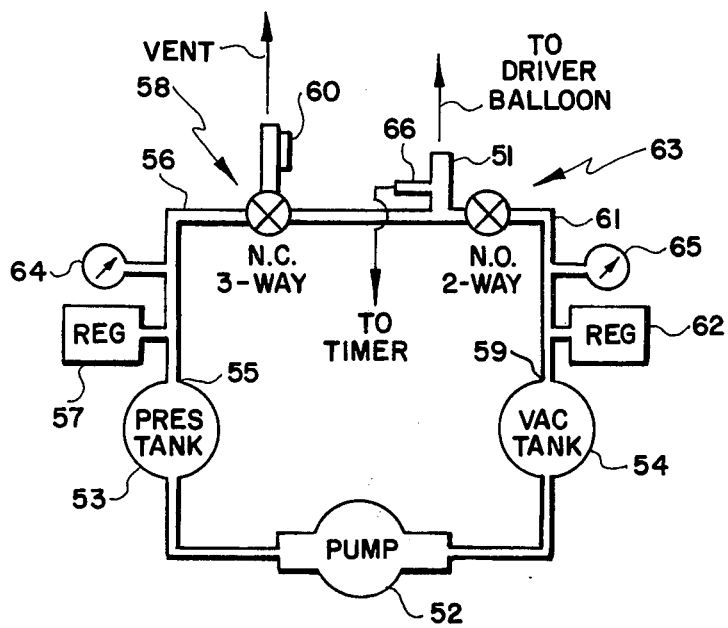
FIG. 7 is a diagrammatic representation of a pressure system for use with the pulsatile pump.

Directing attention now to FIG. 7, there is shown in block diagram form a pneumatic system for controlling the driver balloon 22. The system as shown in FIG. 7 comprises a conventional pump 52 for creating pressure in a pressure tank 53 and a vacuum in a vacuum tank 54. The outlet 55 of the pressure tank 53 is coupled via pressure regulator 57 and line 56 to line 51 connected to the driver balloon and a spring-loaded normally closed solenoid actuated three-way two-positioned valve 58. The three-way valve 58 is controlled by input signals to its solenoid. The inlet 59 of the vacuum tank is also coupled via vacuum regulator 62 and line 61 to line 51 connected to the driver balloon and a spring-loaded normally open solenoid actuated two-way two-positioned valve 63. As with the three-way valve 58, the two-way valve 63 is controlled by input signals to its solenoid.

The normally closed three-way valve 58 in its open or actuated position couples the driver balloon 22 to the pressure tank 53 and in its unactuated position, vents the driver balloon 22 to atmosphere through a one-way check valve 60. The normally open two-way valve 63 in its closed or actuated position isolates the driver balloon 22 from the vacuum tank 54 and in its unactuated position, couples the driver balloon 22 to the vacuum tank 54. Both valves 58 and 63 are simultaneously maintained in either their actuated or unactuated position to provide fail-safe operation. Thus, if power is lost, the driver balloon 22 will be deflated and remain in this condition so that the flow of blood through the blood pumping balloon 21, now fully expanded, will not be impeded. Of course, if desired, venting of the driver balloon 22 may be omitted when it is coupled to the vacuum tank and vice versa. Pressure detectors 64 and 65 are provided in respectively the pressure line 56 and the vacuum line 61 to indicate the pressure therein as determined by setting of the pressure regulators 57 and 62.

Coupled to the pressure line 51 connected to the driver balloon 22 is a pressure detector 66 for effectively sensing the pressure in the driver balloon 22 and providing an electrical signal supplied to a timer 84, one function of which is to cut off the electrical power to the valves 58 and 63 if the driver balloon 22 remains pressurized for more than a predetermined length of time, such as, for example, about 1½ seconds.

Figure 8:
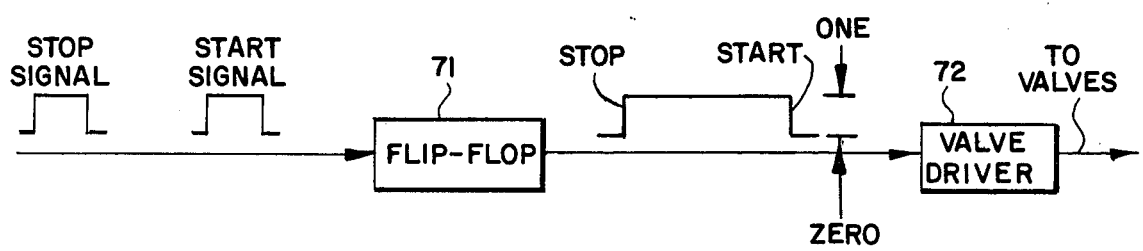
FIG. 8 is a schematic block diagram of circuitry for controlling valves in the pneumatic system for actuating the driver balloon in the pulsatile pump.

In either the total or partial bypass modes, or with the vacuum tank in the system or isolated from it, a "start" signal may be generated in the console 16 or the like to set a flip-flop circuit 71 to one as shown in FIG. 8. The output signal from the flip-flop circuit 71 is fed to a valve driver circuit 72 more fully shown in FIG. 9. In the driver circuit 72 as shown in FIG. 9, a DC signal derived from the flip-flop circuit 71 is fed to a first transistor 75 through a photo-transistor 76 which isolates the valve driver circuit 72 from its input or flip-flop circuit. The output of the first transistor 75 is fed to a second transistor 77 and causes it to become conducting and thereby permit current to flow through the windings of the solenoids 78 and 79 in respectively valves 58 and 63. The valves 58 and 63 are now turned "on" or actuated. After a predetermined interval of time, a "stop" signal is provided to set the flip-flop circuit 71 to zero. The signal to the first transistor 75 will now go to zero, the second transistor 77 will become nonconducting and no current will flow therethrough to the solenoids 78 and 79. Because they are spring-loaded, both valves go to their "off" or unactuated position as soon as the current to their solenoids is cut off. After a further predetermined interval of time, a start signal is again provided to the flip-flop circuit 71 and another cycle begins. Diodes 81 and 82 are provided to prevent ringing.

Switch 83 is provided in series with the solenoid 79 of valve 63 to permit the operator to prevent, if it is so desired, the solenoid 79 from being deactuated and thereby couple the driver balloon to the vacuum tank. Thus, where the switch 83 is in the position as shown in FIG. 9, valve 63 will be controlled by the input signals to the flip-flop circuit 71 and when switch 83 is in its right-hand position, valve 63 will remain actuated and unaffected by the input signals to the flip-flop circuit.

A safety provision now to be described is incorporated in the valve driver circuit 72. The voltage appearing on the collector of the second transistor 77 is supplied to the timer 84. If current flows uninterruptedly through valve solenoid 78 for more than the aforementioned 1½ seconds, a signal is provided by the timer 84 to the normally closed relay 85 causing it to open. When relay 85 opens, the power supply voltage is interrupted, valve 58 will close and valve 63 will open (irrespective of the position of switch 83) and the driver balloon deflates. As noted previously, another feature of the circuit shown in FIG. 9 is that the two-way valve 63 can be locked in the "on" position by means of switch 83 so long as the normally closed relay 85 is not opened by the timer 84. When switch 83 is locked in the on or right-hand position, the vacuum tank is isolated from the system.

FIG. 10 shows an alternate pneumatic system for controlling the driver balloon 22. The pneumatic system of FIG. 10, while utilizing the pump 52, pressure tank 53, pressure line 56, vacuum tank 54, regulators 57 and 62, pressure detector 66 and pressure indicators 64 and 65 of FIG. 7, utilizes only a single three-way valve 91 in combination with safety vent 92 in the vacuum line 61.

For the arrangement as shown in FIG. 10, the valve 91 is simply caused to be switched to its first position to couple the pressure tank to the driver balloon while isolating it from the vacuum tank, and then switched to its second position to couple the driver balloon to the vacuum tank while isolating it from the pressure tank. The safety vent 92 is provided to insure venting of the driver balloon in the event of failure of pump 52. The utilization of the timer 84 and its principle of operation insures that in the event of a power failure, switch 91 will be in its unactuated position coupling the driver balloon to vent 92 and/or vacuum tank 54.

FIG. 11 shows an alternate embodiment of the pulsatile pump wherein an inlet valve 101 and/or outlet valve 102 are provided for cooperation with the blood pumping balloon 21.

Thus, where the pulsatile pump is to be used as a blood pump per se, an inlet valve 101 may be provided in the inlet connector 33 to permit only blood flow into the blood pumping balloon and an outlet valve 102 provided in connector 34 to permit only blood flow out of the blood pumping balloon. With the addition of the aforementioned inlet valve 101 and outlet valve 102, it will be seen that the pulsatile pump will operate to provide pulsatile flow in one direction, thereby permitting the pulsatile pump to function as an extracorporeal blood pump. Provision of the inlet and outlet valves in the connectors permits the pulsatile pump to be easily and quickly modified for different applications by the simple procedure of merely connecting to the housing an appropriate connector or connectors with or without valves as circumstances require.

The various features and advantages of the invention are thought to be clear from the foregoing description. Various other features and advantages not specifically enumerated will undoubtedly occur to those versed in the art, as likewise will many variations and modifications of the preferred embodiment illustrated, all of which may be achieved without departing from the spirit and scope of the invention as defined by the following claims:

I claim:

1. A blood pump comprising:
   (a) an elongated rigid housing having a longitudinal axis, an annular side wall and oppositely disposed first and second end walls defining a closed chamber, said first end wall having a first opening off-set from said housing longitudinal axis and adjacent said side wall, said second end wall having a second opening coaxial with said first opening and one of said end walls having a third opening off-set from said longitudinal axis and adjacent said side wall;
   (b) an elongated flexible blood pumping balloon disposed in said chamber, said balloon having a longitudinal axis, an annular central portion and generally sloping transitional end portions each terminating in a first and second port portion off-set from said pumping balloon longitudinal axis toward said side wall and respectively registering with said first and second openings in said end walls, said sloping end portions facing away from said housing side wall;
   (c) an elongated flexible driver balloon disposed in said chamber in side-by-side and contacting relationship with said blood pumping balloon, said driver balloon having a longitudinal axis, an annular central portion and generally sloping transitional end portions facing inwardly away from said housing side wall and toward said blood pumping balloon sloping end portions, one of said end portions terminating in a third port portion off-set from said driver balloon longitudinal axis toward said side wall and registering with said third opening in said one of said end walls, the transitional end portions of said blood pumping and driver balloons each having a sloping configuration that results in substantially only rolling contact between the said balloons at these end portions;
   (d) first and second connector means sealably carried by respectively said first and second end walls at said first and second openings for coupling said pumping balloon first and second port portions to blood carrying lines;
   (e) third connector means carried by said one of said end walls at said third opening for coupling said driver balloon third port portion to a pressure line; and
   (f) venting means including at least one air passage in said housing for providing communication between the interior of said housing and atmosphere.

2. A blood pump as defined in claim 1 wherein the other of said end portions of said driver balloon includes means for fixedly connecting said other end portion of said driver balloon to said housing whereby substantially only radial expansion and contraction movement of said driver balloon can occur in said housing.

3. A blood pump as defined in claim 1 wherein said venting means is a one-way air valve permitting only gas flow out of said housing.

4. A blood pump as defined in claim 3 wherein the other of said end portions of said driver balloon includes means for fixedly connecting said other end portion of said driver balloon to said housing whereby substantially only radial expansion and contraction movement of said driver balloon can occur in said housing.

5. A blood pump as defined in claim 2 and additionally including a one-way inlet valve operatively associated with said blood pumping balloon first port portion whereby blood may only flow into said blood pumping balloon through said first port portion.

6. A blood pump as defined in claim 5 and additionally including a one-way outlet valve operatively associated with said blood pumping balloon second port portion whereby blood may only flow out of said blood pumping balloon through said second port portion.

7. A blood pump as defined in claim 2 wherein the diameter of said driver balloon is less than the inside diameter of said housing side wall whereby when said driver balloon is inflated to its said diameter, said blood pumping balloon will not be fully deflated and thereby prevent occlusive pumping action by said blood pumping balloon.

8. A blood pump as defined in claim 7 wherein the diameter of said blood pumping balloon is less than the inside diameter of said housing side wall whereby when said blood pumping balloon is inflated to its said diameter, said driver balloon will not be deflated to an extent that results in contact of its interior surface.

* * * * *